United States Patent [19]

Pouletty et al.

[11] Patent Number: 5,420,013

[45] Date of Patent: * May 30, 1995

[54] HLA TYPING

[75] Inventors: Philippe Pouletty, Atherton; Peter Chun, South San Francisco; Chin H. Chang, Los Altos, all of Calif.

[73] Assignee: Sangstat Medical Corporation, Menlo Park, Calif.

[*] Notice: The portion of the term of this patent subsequent to Oct. 26, 2010 has been disclaimed.

[21] Appl. No.: 101,259

[22] Filed: Aug. 2, 1993

Related U.S. Application Data

[63] Continuation-in-part of Ser. No. 745,163, Aug. 15, 1991, abandoned, which is a continuation-in-part of Ser. No. 698,319, May 10, 1991, Pat. No. 5,256,543.

[51] Int. Cl.$^6$ .................. G01N 33/543; G01N 33/577
[52] U.S. Cl. .................................... 435/7.24; 435/7.2; 435/7.21; 435/7.94; 435/962; 435/967; 435/970; 435/975; 436/518; 436/548
[58] Field of Search ...................... 435/7.2, 7.21, 7.24, 435/7.94, 962, 967, 970, 975; 436/518, 548

[56] References Cited

U.S. PATENT DOCUMENTS

| | | | |
|---|---|---|---|
| 4,294,817 | 10/1981 | Burgett et al. | 422/56 |
| 4,722,889 | 2/1988 | Lee et al. | 435/7 |
| 4,722,899 | 2/1988 | Hamaoka et al. | 435/172.2 |
| 4,725,556 | 2/1988 | Mareschal et al. | 436/500 |
| 4,737,456 | 4/1988 | Weng et al. | 435/7 |
| 4,895,706 | 1/1990 | Root et al. | 422/102 |
| 4,937,199 | 6/1990 | Griffiths et al. | 436/511 |
| 5,059,524 | 10/1991 | McKenzie et al. | 435/7.24 |
| 5,098,827 | 3/1992 | Boyle et al. | 435/7.34 |
| 5,256,543 | 10/1993 | Pouletty et al. | 435/7.94 |

FOREIGN PATENT DOCUMENTS 1684683 10/1991 U.S.S.R. .
8705398 9/1987 WIPO .

OTHER PUBLICATIONS

Ferreira et al., *Clin. Chim. Acta.*, 174:207–211 (1988).
Sakaguchi et al., *Human Immunol.*, 21:193–207 (1988).
Trapani et al., *Immunol. Cell Biol.*, 66:215–219 (1988).
Villar et al., *Eur. J. Immunol.*, 19:1835–1839 (1989).

*Primary Examiner*—David Saunders
*Attorney, Agent, or Firm*—Bertram I. Rowland

[57] ABSTRACT

Methods and compositions are provided for detecting HLA polymorphs where distinguishing antibodies are not readily available. Cross-reactive antibodies are employed, where one cross-reacts with the HLA of interest and other alleles, and the other cross-reacts with one of the other alleles, but not with the HLA of interest. By appropriate protocols and controls, the polymorph of interest may be detected.

11 Claims, No Drawings

HLA TYPING

CROSS-REFERENCE TO RELATED APPLICATIONS

This application is a continuation-in-part of application Ser. No. 07/745,163, filed Aug. 15, 1991 and now abandoned, which is a continuation-in-part of Ser. No. 07/698,319, filed May 10, 1991 now U.S. Pat. No. 5,256,543, issued Oct. 26, 1993.

INTRODUCTION

1. Technical Field

The technical field of this invention is HLA typing.

2. Background

There is substantial interest in being able to type human leukocyte antigens (HLAs) for a variety of reasons. In many situations it has been found that specific HLA alleles may be associated with a susceptibility to a particular disease. For example, HLA-B27 has been associated with ankylosing spondylitis and related diseases. When transplanting organs to a host it is desirable that the organs be matched, so as to minimize the risk of rejection. HLA typing may also find application in determining lineage, epidemiology and the like.

There is an extensive family of HLA antigens divided into Class I and Class II. In each of the classes, there are polymorphic regions. These sites may or may not provide for epitopes which will induce an immune response which will allow for the preparation of antisera or monoclonal antibodies which are specific for a specific HLA allele and able to distinguish that HLA allele from other HLA allele.

This situation is exemplified by the cross-reactivity between HLA-B27 and HLA-B7 where monoclonal antibodies are not readily available which are specific for HLA-B27, so as not to cross-react with HLA-B7 or other HLA allele.

Since mammals are diploid, there will be pairs of HLA antigens as to each of the particular groups. Thus, unless one can determine specifically a particular HLA allele, one cannot be certain whether there are two different alleles or one is observing cross-reactivity. There is, therefore, substantial interest in developing methods which will allow for the accurate detection of a particular HLA allele, where substantial cross-reactivity is observed with other HLA alleles.

RELEVANT LITERATURE

Sakaguchi et al, *Human Immunology*, 21:193–207 (1988) describes use of monoclonal antibodies in determination of HLA-B27 and a double determinant immunoassay for detection of HLA-B27. Villar et al., *Eur. J. Immunol.* 19:1835–39 (1989) describe the detection of Class I molecules from a variety of sources. Toxiadis and Grosse-Wilde, Vox Sang 56:196-99 (1989) describe the detection of HLA Class I proteins. Ferreira et al., *Clin. Chim. Acta.* 174:207–11 (1988) describe the use of a solid-phase enzyme immunoassay for detection of HLA Class I antigens in sera.

SUMMARY OF THE INVENTION

Methods and compositions are provided for detecting closely related alleles employing immunoassays, where there is no available antibody to distinguish between two alleles. The method and compositions find specific exemplification in relation to distinguishing the HLA alleles B27 and B7, where B27 is of diagnostic interest. One method employs using an antibody specific for one of the alleles, but not the other, to remove that allele and then using the cross-reactive antibody to detect the other allele. A second method employs a sandwich assay, where separate wells have a cross-reactive antibody in one well and an antibody specific for one of the alleles in the other well. By appropriate use of controls and measurement of signals in the different wells, a cutoff value is determined which allows for the accurate determination of the presence or absence of the allele.

DESCRIPTION OF THE SPECIFIC EMBODIMENTS

Methods and compositions are provided for the accurate detection of one of two polymorphic antigens in a sample, where the antigens are characterized by having no useful receptor readily available to distinguish between the two antigens, the antigens are members of a much larger group of antigens, usually substantially in excess of 10, where there is substantial cross-reactivity between the antigens in sharing numerous epitopes, and differences between the antigens may be subtle, involving only one or a few amino acids.

Two different techniques are employed for the determination of the allele for which no specific monoclonal antibody exists or is not readily available. The first way is to employ a separation, where an antibody which binds in a concentration range to only one but not both of the alleles is employed for removing the complementary allele from the sample. The cross-reactive monoclonal antibody, which cross-reacts with the two alleles, may then be used to determine the allele for which a specific antibody is not available.

In a second way, sandwich immunoassays are employed, where one employs negative and positive controls, as well as two additional wells, one well having the cross-reactive antibody and the other well having an antibody which reacts with only one of the two cross-reactive alleles, preferably unreactive with other alleles or reactive with only one or a few rare alleles. One then adds labeled antibody which is cross-reactive with both of the alleles, and obtains values of the level of label present in the various wells for the two controls and the two sample wells and any additional repeat wells. Using the values obtained, one obtains a cutoff value which is twice the value of the well with the antibody which is cross-reactive with the two alleles divided by the value of the well which is specific for the cross-reactive antigen, using a known amount of the cross-reactive antigen, an amount approximating the amount which is in the range normally encountered in samples. Values for the sample above the cutoff value indicate the presence of the particular allele.

The separation methodology will be considered first. Exemplary of this situation is the detection of HLA-B27 where the subject invention provides a simple and efficient way, particularly without requiring special equipment for carrying out the process or detecting the result. The method employs as a first stage, using a binding moiety, usually a monoclonal antibody, to specifically deplete HLA-B7 antigen from a sample to a non-interfering level, particularly a blood sample or sample derived therefrom. The resulting HLA-B7 depleted medium is then combined with a second binding moiety, usually a monoclonal antibody, which has a high affinity for B27 and B7. Formation of immune complexes between the binding moiety and any B27 present is detected as indicating the presence of soluble B27 in the sample.

Any binding moiety binding to the target antigen(s) or having the requisite discrimination as to the different HLA alleles may be used. Binding moieties include antibodies, any of the isotypes, e.g., IgG, IgM, etc., fragments thereof, e.g. Fab, F(ab')$_2$, Fv, etc., binding peptides, T-cell receptors, or the like. For the most part, monoclonal antibodies are the most convenient and exemplify the problem of cross-reactivity, where the available monoclonal antibodies in relation to HLA-B27 are unable to specifically distinguish this allele from other alleles. It is understood that in referring to monoclonal antibodies, other binding moieties having analogous cross-reactivities may be substituted.

In the first step, the sample, normally blood, serum, plasma or urine, may be subjected to prior treatment such as dilution in buffered medium, concentration, filtration, or other gross treatment which will not involve any specific separation. The sample can be relatively small, generally being not less than about 1 $\mu$l and will generally not exceed about 500 $\mu$l, generally being in the range of about 10 to 200 $\mu$l. Dilution will usually not be more than 5-fold, more usually not more than 2-fold and concentration will normally not be necessary.

The sample is then contacted with an antibody which is reactive with HLA-B7, but not significantly reactive with HLA-B27, but may be cross-reactive with any other HLA allele. The significant factor for the antibody is that it can distinguish between HLA-B7 and HLA-B27. While many antibodies which ostensibly have this capability, may not prove to be satisfactory, there are a number of antibodies in the ATCC catalog, as well as catalogues of other repositories, which are satisfactory. As appropriate, purified polyclonal antisera may be employed, where the antisera is prepared in response to HLA-B7 and then purified to ensure that any antibodies cross-reactive between HLA-B7 and HLA-B27 are removed. This can be achieved by passing the antisera through an affinity column comprising HLA-B27 randomly attached to a support, such as agarose, Sephadex, polystyrene beads, magnetic beads, nylon membranes or the like. The eluent may then be assayed for its ability to bind to soluble HLA-B27.

The sample may be passed through an affinity column comprising anti-HLA-B7 bound to a support, may be mixed with anti-HLA-B7, directly or indirectly, covalently or non-covalently bound to beads or particles, e.g., magnetic particles, may be mixed with anti-HLA-B7 and contacted with, in a column, microtiter well, or other container, anti-mouse (or other species) Ig antibody bound to a support, where the anti-HLA antibody is a mouse (or other species) antibody, or may be mixed with anti-HLA-B7, conjugated with a ligand, e.g., biotin, followed by contacting with avidin, or streptavidin ("strept/avidin") bound to a support as described above. (By "directly or indirectly is intended that the molecule in question e.g., anti-HLA-B7, is either directly bound to the solid support e.g., covalently through a spacer arm or is bound to an intermediate molecule directly bound to the solid support, e.g., an antibody to the molecule in question.) In each situation, the mixture is contacted or incubated for sufficient time with sufficient amount of the anti-HLA-B7 to provide for substantial complex formation of the anti-HLA-B7 and separation of the HLA-B7-anti-HLA-B7 complex from the sample medium.

Of particular interest is the use of an affinity column employing a receptor bound to a support, conveniently a polysaccharide, more particularly Sepharose. The Sepharose may be activated by any convenient means, such as cyanogen bromide, carbodiimide, bromoacetyl, p-carboxyphenacyl bromide, or the like. The receptor may then be conjugated to the support in accordance with conventional ways, depending upon the nature of the functionality bound to the support. Cyanogen bromide and other active halides do not require any activation, while carboxyl groups may be activated with carbodiimide. After reacting the activated support with the antibody, any unreacted functionalities may be terminated with an alkanolamine, e.g., ethanolamine. The amount of antibody will generally be from about 0.2–2 mg/0.5 ml of packed gel.

Alternatively, 1–5$\mu$ magnetic beads coated with anti-HLA-B7 antibody ($10^6$–$10^7$ beads) are incubated with a serum or other specimen e.g., 100 $\mu$l, for 5–30 min at ambient conditions. The beads may be separated using a magnetic filter, a solenoid or the like.

Once the sample has been at least substantially depleted of any HLA-B7 which may have been present, the sample may now be assayed for the presence of B27. Various assays may be employed for detection of the presence of HLA-B27. A number of STAT assay protocols may be employed, as desired. Of particular interest is the use of a STAT test cartridge as described in U.S. application Ser. No. 644,941, filed Jan. 23, 1991, now U.S. Pat. No. 5,147,780, issued Sep. 15, 1992. This assay employs a porous filter having measuring regions which are separated by nonporous regions. The filter or membrane is supported by an absorbent layer, which serves to absorb the sample and provides for flow of the sample through the membrane. Desirably, the membrane and absorbent layer are separated by a flow control layer, which may assume various characteristics. Depending upon the nature of the membrane, the membrane may be coated on the fluid exiting side with a coating which will substantially reduce the pore size of the membrane.

Various membranes may be employed, although it is found that glass fiber membranes and nylon membranes appear to be substantially superior to other types of membranes. Conveniently, the glass membrane may be sprayed with an acrylic polymer, which does not interfere with the assay procedure, but provides for the desired flow rate. The amount of acrylic polymer which is applied may be determined empirically, although generally the amount will be in the range of about 0.1 to 1 mg/cm$^2$ with a glass membrane having a pore size in the range of about 0.2 to 5$\mu$. The separation of the various measurement regions may be achieved by using non-porous tape or other convenient barrier. In addition, strips may be provided over the barrier to provide a visual indication of the areas in the different regions.

For each sample, there will be desirably three regions having capture antibodies: (1) a procedural positive region coated with an anti-immunoglobulin antibody specific for the antibody conjugate which binds to the HLA-B27 or coated with an anti-Ig where the Ig is of the isotype of the anti-HLA-B27; (2) a test region coated with a monoclonal antibody which is cross-reactive with HLA-B27 and HLA-B7, but not cross-reactive with other HLAs; and (3) a negative procedural region coated with the same anti-HLA-B7 monoclonal antibody as used for depleting HLA-B7. A specimen which is HLA-B27 positive shows color development in the first two wells but not the third; a specimen which is HLA-B7 positive and HLA-B27 negative, where the HLA-B7 has been properly depleted or a HLA-B7/B27 negative specimen, would only show a positive result in the first region; and a specimen which is B7 positive and has not been properly absorbed will be sensitive in all three regions.

The second methodology will have many similarities to the first methodology and may use similar reagents. The method employs two series of sample wells, a first series using as the capture antibody the cross-reactive antibody and a second series using as the capture antibody the antibody which binds to only one of the two alleles, but may bind to other rare alleles. The specimens may be whole blood from which the serum is separated, plasma specimens containing heparin, EDTA or ACD as an anti-coagulant, cerebral spinal fluid ("CSF") specimens, or cell culture supernatant specimens. The specimens may be stored undiluted up to 24 h at room temperature, one week between 2°-8° C., frozen at −20° C. or below, if longer storage is required.

Various devices may be used in which to carry out the assay, such as strips, microtiter well plates, slides, test tubes, STAT cartridges, and the like. Since small volumes will be used and repetitive washes will be employed, the devices employed should allow for concentration of the reagent providing the detectible signal as well as absorption or removal of washed solutions.

The materials employed will include the device comprising a plurality of wells or spots which have one or the other antibody bound thereto in a predetermined amount. The amount should be sufficient to bind enough of the allele to be determined to allow for detection of the allele. This can be readily determined empirically. A positive control is provided, which comprises the allele in an appropriate buffer at an appropriate concentration in relation to the amount of allele which would be expected to be present in a positive sample. For example, for determinin B27 allele, the amount of B7 allele which is present will range from about 30 ng/ml to 1 μg/ml. A negative control will be provided, which will be buffer.

To carry out the assay, one may add the positive control and the negative control to one or more wells or sites with each of the antibodies. Desirably, one will have two wells or sites for each determination, so that an average value can be determined for the positive and negative controls. The specimen may then be added to one or more wells with each of the antibodies. Generally, the specimen volume will be in the range of about 20 to 200 μl, more usually about 20 to 100 μl, where the specimen will normally be used neat or prediluted in a buffered solution. The sample is then incubated for sufficient time to ensure complete binding. Usually, the incubation will be at least about 15 min, more usually at least about 30 min and generally not more than about 6 h, usually not more than about 4 h. For the most part, 2 h has been found to be adequate. The incubation may be carried out at ambient temperatures. At the end of the incubation, any liquid present is removed and the wells or sites thoroughly washed, conveniently with deionized water. Usually, at least about two washes will be used, where the total number of washes may be five or more. Where wells are employed, the well may be filled with the wash solution, allowed to stand, then decanted and the process repeated.

A labeled conjugate may then be added to the wells or sites. The label may be an enzyme, radioisotope, fluorescer, chemiluminescer, etc. Desirably, the label will be an enzyme. The antibody will be specific for an epitope common to the alleles. In the case of Class I HLA, the antibody may be conveniently to β2-microglobulin. Alternatively, the antibody could be to the constant region, or in the case of two alleles, to a common epitope, other than the epitope to which the capture antibody binds. Again, the assay mixtures may be incubated for sufficient time for binding, usually at least 0.5 h, and not more than about 3 h, 1.5 h usually sufficing. Ambient temperatures may be employed. The complexes of antibody and antigen are then thoroughly washed, similarly to the wash procedure used previously.

With an enzyme conjugate, a substrate solution is then added to the wells or sites and the reaction allowed to proceed for a predetermined time, generally at least about 5 min and not more than about 1 h. A stop solution may then be added, which terminates the reaction, without being detrimental to the detection of the dye which has formed from the substrate. Depending upon the nature of the enzyme product or other label which is present, one may then determine the amount of detectable label or product which is present. One may use spectrophotometers, fluorimeters, light scattering devices, or the like.

One then analyzes the results as follows. The values for the various determinations may be divided as follows: positive and negative controls for the B7/B27 assays; positive and negative controls for the B7 assays; and the specimen values in the B7/B27 and B7 assays. One determines the various values one would expect using specimens of known value, so that one can identify ranges in which the various values will fall if the assay is operative. For example, in the assay described in the experimental section, values for the specimen in the B7 assay should not exceed two and the ranges for the negative controls and positive controls for the B7/B27 and B7 assays can also be determined. In addition, one can determine the range for the value obtained with the B7/B27 assay divided by the value obtained for the B7 assay. Thus, one can have security in the operability of the assay, by a virtue of the individual values falling within predetermined ranges.

A discrimination value is employed which is the value obtained for the negative control for the B7/B27 assay (no B7 present) plus a percent, generally in the range of about 10-30%, of the value obtained for the positive control in the B7/B27 assay (B7 present). Thus, the value obtained for the sample in the B7/B27 assay must exceed such discrimination value or the sample may be considered to be HLA/B27 negative.

If the specimen value exceeds the discrimination value, then further calculation must be performed. The B7 cut-off value or minimum value for a positive B7 result is obtained by multiplying the quotient of the positive control of the B7/B27 assay divided by the positive control of the B7 assay times two. If the quotient of the value obtained with the specimen of the B7/B27 assay divided by the B7 assay is equal to or greater than the B7 cut-off, then the specimen is HLA-B27 positive. Otherwise, the specimen is B27 negative.

Paper can be supplied having the appropriate legend or a simple algorithm, which will allow for the rapid determination of a positive or negative result. Thus, the reading device may be connected with a computer, which will allow for a direct readout, without requiring any manual computation.

The following examples are offered by way of illustration and not by way of limitation.

EXPERIMENTAL

Example 1

HLA B27 Test

1. To 100 μl of patient serum add 1–4 μl of 0.5 mg/ml mouse IgG anti-B7 antibody which cross-reacts with HLA-B7 and HLA-B40, but does not react with HLA-B27 (Incstar Corporation). Vortex and incubate at room temperature for 5–10 minutes.

2. Add 200–600 μl of magnetic beads coated with goat anti-mouse IgG (Advanced Magnetics, Inc., Catalog No. 4340D) to the above mixture. Cap the tube and mix on a rocker at room temperature for 20–30 minutes.

3. Place the tube on the surface of a strong magnet in upright position for 2–4 minutes to completely bring down all magnetic beads.

4. Transfer 200 μl of the supernatant to the STAT cartridge (SangStat Medical Corp., Menlo Park, Calif.). Allow to drain completely. [STAT cartridge containing 3 miniwells (A, B, C) with nylon membrane coated with antibodies at a concentration of 1 mg/mL in 0.1M PBS pH 7.2. Miniwell A coated with mouse anti-goat antibody (Jackson Laboratories) diluted 1:50 in normal goat serum. Miniwell B coated with mouse IgG anti-HLAB7/B27 monoclonal antibody (Clone SV90.1). Miniwell C coated with the mouse IgG HLA B7/B40 specific monoclonal antibody (Incstar Corporation)].

5. Add 200 μl of antibody conjugate (anti-beta-2 microglobulin goat antibody conjugated to alkaline phosphatase, diluted to 5 μg/mL in 0.1M PBS pH 7.2 containing 1% casein an 0.1% Tween 20) to the STAT cartridge. Allow to drain completely.

6. Add 1 mL of wash solution (0.1M PBS pH 7.2 with 0.1% Tween 20) to each cartridge. Allow to drain completely.

7. Add 200 μl of chromogenic substrate (BCIP/NBT substrate solution) (SangStat Medical Corporation). Allow to develop for 3–4 minutes.

8. Read results.

INTERPRETATION OF TEST RESULTS

The development of blue-grey rings in the first miniwell only (miniwell A) is a negative test for HLA-B27.

The development of blue-grey rings in the first (A) and second (B) miniwells, with the third (C) miniwell showing no rings or lighter rings than in the second (B) miniwell, is a positive test for HLA-B27.

QUALITY CONTROL

If there is no color development in the first miniwell (Miniwell A, positive procedural reference) or uniform color development in all miniwells, the test is invalid.

Color development in miniwell C indicates that removal of HLA-B7 (or B40) was incomplete or that there is an interference which may be related to anti-mouse IgG antibodies in the serum specimen.

RESULTS

Thirty specimens collected from individuals previously phenotyped by microcytotoxicity assay were tested by the rapid assay (HLA-B27).

| HLA B27 STAT | CYTOTOXICITY | | | |
|---|---|---|---|---|
| | B27+/B7+ | B27+/B7− | B27−/B7+ | B27−/B7− |
| Positive | 4 | 10 | 0 | 0 |
| Negative | 0 | 0 | 5 | 15 |
| Invalid | 0 | 0 | 1 | 0 |

A preferred embodiment is to have the immunoglobulins as one or more circles, where there is a concentration gradient from the center outward. Particularly desirable is to have a relatively high immunoglobulin concentration central region and a substantially lower concentration outer periphery. This embodiment is described in U.S. application Ser. No. 664,941 filed Jan. 23, 1991, now U.S. Pat. No. 5,147,780, issued Sep. 15, 1992. The concentration gradient can be readily achieved by using a porous pointed stub which is pressed against the membrane, so that a significant proportion of the immunoglobulin present in the sample becomes bound around the stub point creating a relatively high concentration in a central region and a substantially lower concentration around the central region.

The rate of flow of the sample through the membrane will provide for at least about 10 to 120 sec for contact of the sample with the antibody on the membrane. Similarly, the rate of flow and volume of the enzyme conjugate will allow for 10 to 120 sec of contact with the enzyme conjugate in the various regions. Finally, the rate of flow and volume of the substrate will allow for 10 to 120 sec of reaction of the enzyme with the substrate.

Conveniently, kits may be provided comprising a STAT test cartridge having the three regions described above, the packing for the column, the enzyme conjugate, and, as appropriate, other reagents such as wash solutions, enzyme substrate and the like.

EXAMPLE 2

A kit is employed which comprises a strip of wells coated with mouse IgG monoclonal antibody (KS4) which cross-reacts with HLA-B27 and HLA-B7, and a second strip which is coated with mouse IgG monoclonal antibody (NB40), that reacts with HLA-B7, but not HLA-B27. A positive control containing 1.26 μg/ml of monomorphic HLA-B7 in RPMI/BSA buffer and a negative control (buffer) are provided. The controls and specimens are placed in wells of each of the strips at the same time and allowed to incubate for 2 h at room temperature.

After the incubation, the solutions are aspirated from each of the wells, and each of the wells is washed by filling the well with deionized water, emptying the well and repeating the wash cycle five times. After aspirating the well for the last time, 100 μl of an HRP-(goat anti-$\beta_2$ microglobulin antibody) conjugate (excess antibody) is added to each well. After incubating for 90 min at room temperature, the conjugate solution is aspirated from each of the wells, the wells washed as above and 100 μl of 1 mg o-phenylene diamine in buffer is added to each solution and the reaction allowed to proceed for 30 min. The reaction is kept in the dark. At the end of the reaction, 100 μl of a stop solution (1N HCl) is added. The absorbance of each well at 490–495 nm is read within 5–8 min after adding the stop solution.

Interpretation of assay results
Definitions

| | | | | | | |
|---|---|---|---|---|---|---|
| Black strips = B27/B7 assay | | | | | | |
| Clear strips = B7 assay | | | | | | |
| A = Absorbance value (490–498 nm) | | | | | | |
| PC = | Positive control | PC1 = | Positive control B7/B27 assay | APC1 = | Absorbance value Positive control B7/B27 assay | |
| NC = | Negative control | NC1 = | Negative control B7/B27 assay | ANC1 = | Absorbance value Negative control B7/B27 assay | |
| PC = | Positive control | PC2 = | Positive control B7 assay | APC2 = | Absorbance value Positive control B7 assay | |
| NC = | Negative control | NC2 = | Negative control B7 assay | ANC2 = | Absorbance value Negative control B7 assay | |

A1 = Absorbance value (mean value) of a specimen in the B7/B27 assay
A2 = Absorbance value (mean value of a specimen in the B7 assay
A1/A2 = Specimen Absorbance ratio = Absorbance value (mean value) in the B7/B27 assay divided by Absorbance value (mean value) in the B7 assay (1) Determining mean absorbance values:

Average the duplicate absorbance (A) for the Positive Control (PC), Negative Control (NC) and each specimen in respective assays (the B7/B27 assay [A1-]and the B7 assay [A2]individually). If any specimen shows A>2.0 in the B7 assay, it must be tested again in both assays after predilution (1:2) with the Negative Control.

(2) Validate the assay run:

B7/B27 assay: ANC1 must be less than 0.04 and APC1 must be between 0.1–0.7. B7 assay: ANC2 must be less than 0.04 and APC2 must be between 0.5–2.0. Calculate the ratio APC1/APC2 APC1/APC2 must be between 0.1–0.6.

(3) Calculate the Discrimination Value of the B7/B27 assay (DV1):

DV1=ANC1+20% APC1

(4) Compare the absorbance of each specimen in the B7/B27 assay (A1) with DV1:

If A1<DV1, the specimen is HLA-B27 negative If A1≧DV1, proceed with step (5)

(5) Calculate: APC1/APC2:

Calculate the B27 cutoff: B27 cut-off=2×APC-1/APC2 Calculate the absorbance ratio (A1/A2) for each specimen Compare A1/A2 to the B27 cut-off: If A1/A2≧B27 cut-off, the specimen is HLA-B27 positive If A1-/A2<cut-off, the specimen is HLA-B27 negative In a survey of 110 patient specimens composed of various phenotypes, it was demonstrated that the ratio of the absorbance of the values obtained with the B7/B27 antibody and the B7 antibody is a uniquely specific parameter that can readily screen out the HLA-B27 associated phenotype with a very high degree of accuracy. Table

| HLA-PHENOTYPES | sHLA-STAT ™ B27 Positive | B27 B27 Negative |
|---|---|---|
| B27+/B7− | 28 | 1 |
| B27+/B7+ | 18 | 0 |
| B27−/B7+ | 0 | 42 |

It is evident from the above results, that the subject procedure provides for a simple effective method to accurately determine the B27 HLA type of an individual, without interference from other HLAs. Thus, a rapid diagnosis may be made of an individual's propensity to certain diseases or HLA type for forensic medicine or other purpose. The procedure is simple, does not require sophisticated equipment for performance or measurement and can be easily carried out by unsophisticated operators.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for determining the presence in a physiological sample of a first antigen in the potential presence of a second antigen, where said first and second antigens are characterized by being members of a polymorphic group of alleles which share numerous epitopes, wherein a combination of monoclonal antibodies is used, a first antibody which is cross-reactive to both antigens, but not other common members of said group of alleles, and a second antibody which binds to only said second antigen of said first and second antigens, said method comprising:

combining said sample with said second antibody bound to a solid support to form a liquid assay medium and depleting said second antigen by separating said liquid assay medium from said solid support;

combining said second antigen depleted sample with three different antibodies bound separately to three different solid supports; a first support having an anti-first species antibody of a second species; a second support having said first antibody; and a third support having said second antibody;

adding to said first, second and third supports an enzyme conjugate of a first species antibody binding to an epitope common to all members of said polymorphic group of alleles with said first and second antigens, followed by adding a substrate producing a detectable product; and determining the presence of enzyme as to each of said first, second and third supports by means of said detectable product, wherein a negative value of said fast support indicates the assay method failed;

a positive value of said second support as compared to said third support indicates the presence of said first antigen.

2. A method according to claim 1, wherein said first antigen is HLA-B27 and said second antigen is HLA-B7.

3. A method according to claim 2, wherein said enzyme conjugate is a conjugate of horse radish peroxidase and anti-$\beta_2$-microglobulin.

4. A method according to claim 2, wherein said first, second and third supports comprise a porous membrane to which said antibodies are bound.

5. A method for determining the presence in a physiological sample of HLA-B27 antigen in the potential presence of HLA-B7 antigen, wherein a combination of monoclonal antibodies is used, a first antibody which is cross-reactive to both antigens, but not other common alleles of HLA antigens and a second antibody which binds to only said HLA-B7 of said HLA-B7 and B27 antigens, said method comprising:

combining said sample with said second antibody bound to a solid support to form a liquid assay medium and depleting said HLA-B7 by separating said liquid assay medium from said solid support;

combining said HLA-B7 depleted sample with three different monoclonal antibodies bound separately to three different solid supports comprising a porous membrane; a first support having an anti-first species antibody of a second species; a second support having said first antibody; and a third support having said second antibody;

adding to said first, second and third supports a horse radish peroxidase enzyme conjugate of a first species antibody binding to HLA antigens, washing said supports, followed by adding a substrate producing a detectable product; and determining the presence of enzyme as to each of said first, second and third supports by means of said detectable product;

wherein a negative value of said first support indicates the assay method failed;

a positive value of said second support as compared to said third support indicates the presence of said HLA-B27 antigens.

6. A method for determining the presence in a physiological sample of a first antigen in the potential presence of a second antigen, where said first and second antigens are characterized by being members of a polymorphic group of alleles which share numerous epitopes, wherein a combination of monoclonal antibodies is used, a first antibody which is cross-reactive to both antigens, but not other common members of said group of alleles and a second antibody, which binds to only said second antigen of said first and second antigens, said method comprising:

combining said sample, a negative control free of said members, and a positive control comprising said second antigen with first and second solid supports in separate assay media, said first support comprising said first antibody and said second support comprising said second antibody;

washing said supports free of non-specifically bound components of said sample;

adding an enzyme conjugate of an antibody binding to an epitope common to all members of said group of alleles with said first and second antigens, followed by addition of a substrate producing a detectable product;

determining the amount of enzyme as to each of said assay media by means of said detectable product;

wherein a value for said sample less than the value obtained for the negative control with the cross-reactive antibody plus a predetermined amount equal to about 10 to 30% of the value obtained for the positive control is negative for said first antigen;

a value for said sample at least twice the quotient of the value for the positive control with said first antibody divided by the value for the positive control with said second antibody is positive for said first antigen.

7. A method according to claim 6, wherein said first antigens is HLA-B27 and said second antigen is HLA-B7.

8. A method according to claim 7, wherein said enzyme conjugate is a horse radish peroxidase conjugate with anti-$\beta_2$-microglobulin.

9. A membrane comprising at least three regions: a first region to which is bound a first monoclonal antibody cross-reactive with HLA-B7 and HLA-B27, but substantially not cross-reactive with other HLA antigens; a second region to which is bound a second monoclonal antibody reactive with HLA-B7, but not HLA-B27; and a third region to which is bound antibody specific for immunoglobulin from a predetermined species.

10. A kit comprising the membrane according to claim 9 and an enzyme conjugate of an antibody cross-reactive with HLA-B7 and HLA-B27.

11. A kit comprising an enzyme-monoclonal antibody conjugate binding to a common Class I HLA epitope; and a plurality of wells, one set or wells coated with a first monoclonal antibody binding to HLA-B27 and HLA-B7, but not other HLA alleles, a second set of wells coated with a second monoclonal antibody binding to HLA-B7, but not HLA-B27.

* * * * *